United States Patent [19]

Richards

[11] 4,167,672
[45] Sep. 11, 1979

[54] METHOD AND APPARATUS FOR DEMONSTRATION OF ARBITRARY SURFACES WITH DYNAMIC TOMOGRAPHY

[76] Inventor: Albert G. Richards, 395 Rock Creek Dr., Ann Arbor, Mich. 48104

[21] Appl. No.: 871,287

[22] Filed: Jan. 23, 1978

[51] Int. Cl.² ............................................. G03B 41/16
[52] U.S. Cl. ................................ 250/445 T; 250/473; 250/475 R
[58] Field of Search .................... 250/445 T, 473, 475

[56] References Cited

U.S. PATENT DOCUMENTS

| 3,499,146 | 3/1970 | Richards | 250/445 T |
| 3,742,236 | 6/1973 | Richards | 250/445 T |
| 3,818,220 | 6/1974 | Richards | 250/445 T |

*Primary Examiner*—Craig E. Church
*Attorney, Agent, or Firm*—Reising, Ethington, Barnard, Perry & Brooks

[57] ABSTRACT

A method and apparatus for demonstrating and recording an image of a surface of arbitrary shape and orientation within a body based on a set of tomographic records taken from a radiographic examination of the body. The tomographic records are overlaid on one another in superimposed relation, and then laterally shifted in concert with one another to bring into virtual focus a continuous succession of laminar images through the depth of the body. As the image of each successive body plane or lamina comes into focus, that part of the image that represents the intersection of the arbitrary surface with the imaged body plane or lamina is selected by masking out the remainder of the focused image. As the focusing progresses through the depth of the body, the entire arbitrary plane is demonstrated, and may be recorded by electronic or photographic means.

15 Claims, 14 Drawing Figures

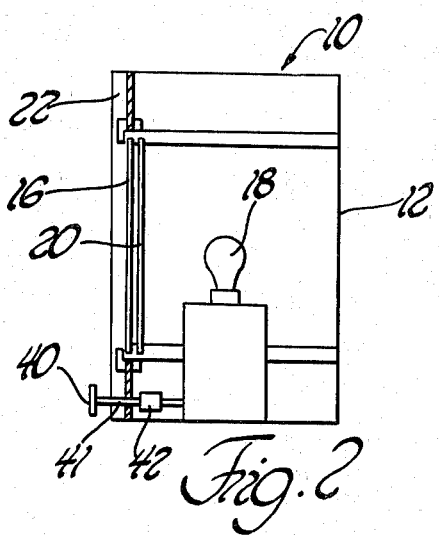
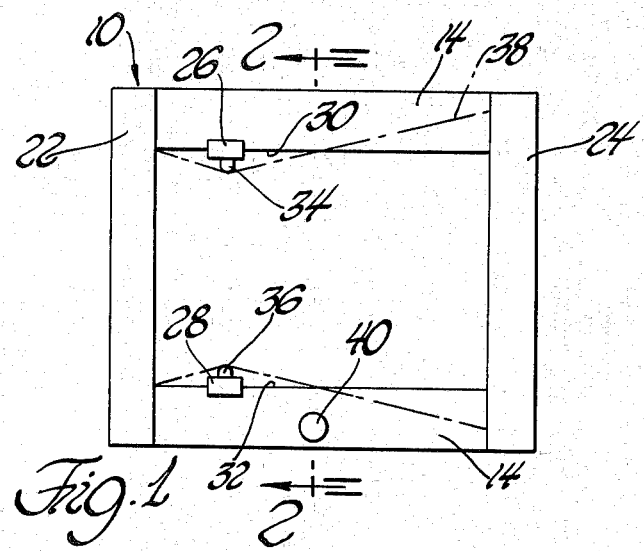
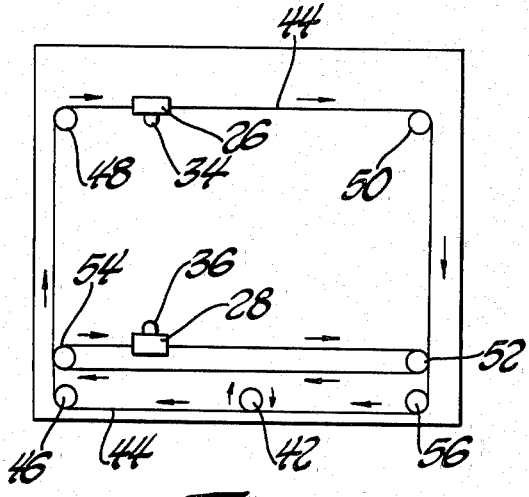
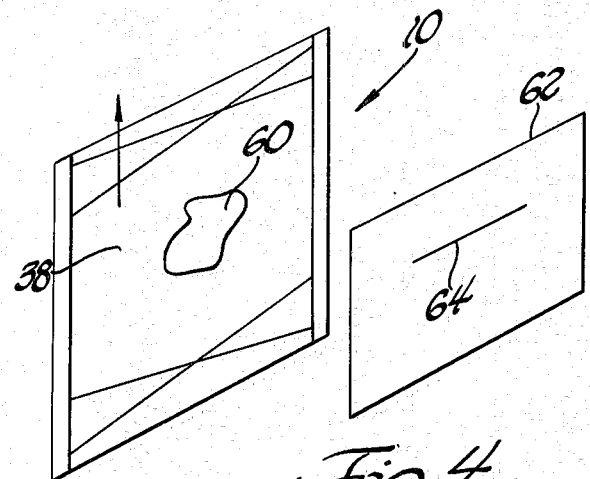
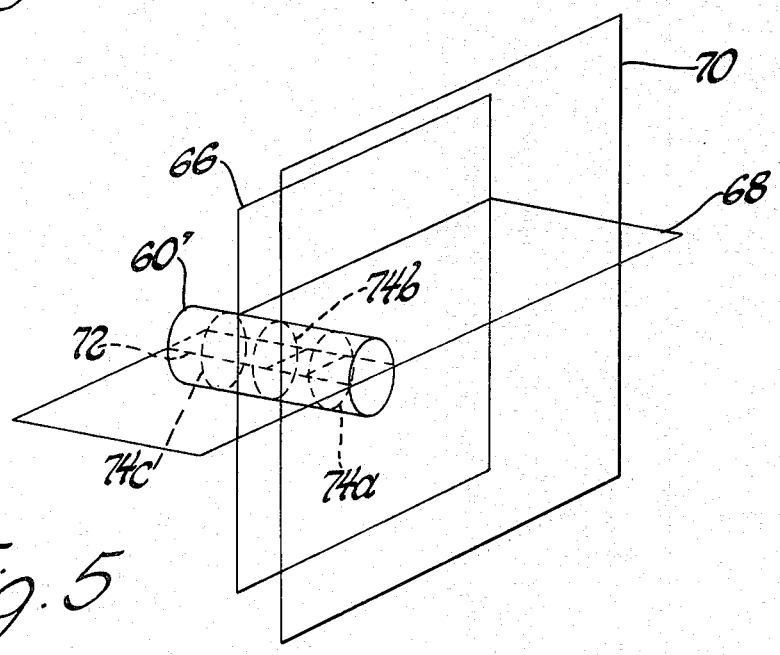

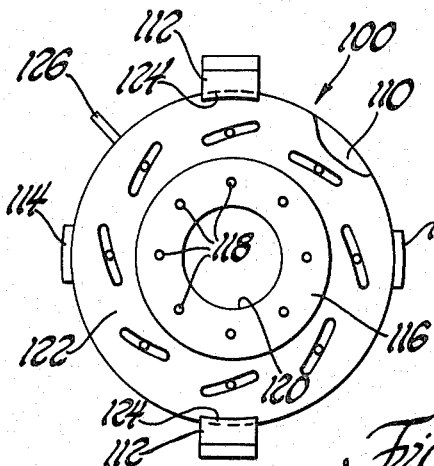
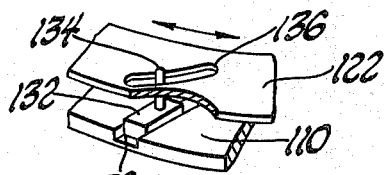
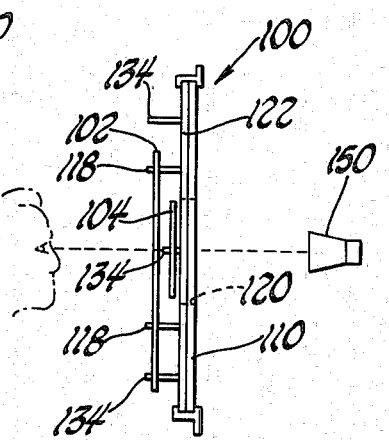
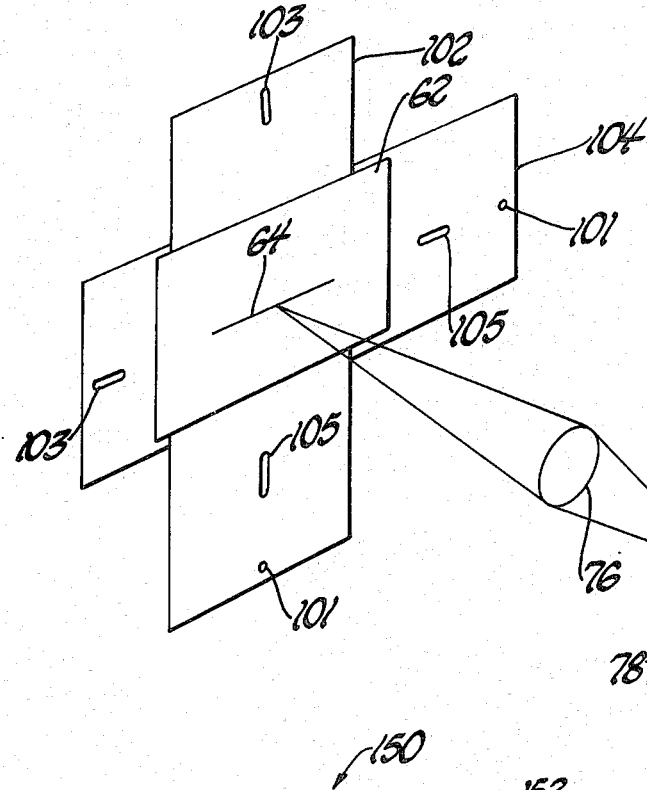
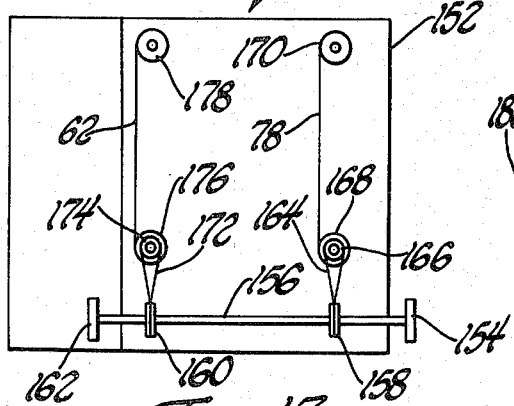
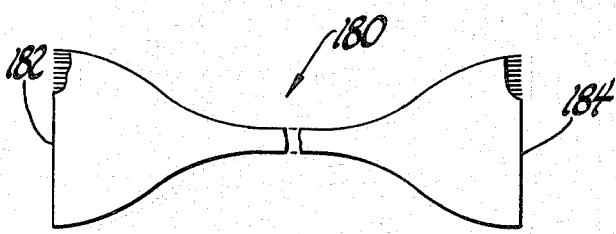

METHOD AND APPARATUS FOR DEMONSTRATION OF ARBITRARY SURFACES WITH DYNAMIC TOMOGRAPHY

TECHNICAL FIELD

The present invention relates to dynamic tomography, and more particularly to a method and apparatus for using dynamic tomography to obtain demonstration and recordation of surfaces of arbitrary shape and orientation within a body or object.

BACKGROUND ART

Dynamic tomography is a technique for producing a set of radiographic records of an object which, when properly combined, enable the reproduction of images of any selected plane or lamina within the volume of interest in a manner which obliterates interfering shadows and thus produces a virtual focus of the image of the selected plane. Dynamic tomography, which is sometimes referred to as varible depth laminagraphy, is described in U.S. Pat. No. 3,499,146 granted to Albert G. Richards on Mar. 3, 1971 for "Variable Depth Laminagraphy with Means for Highlighting the Detail of Selected Lamina."

As described in this reference, dynamic tomography is carried out by a tomographic movement of an X-ray source and film, with the effective pivot point of the linkage between the source and film being disposed in a plane through the object under examination. Multiple exposures are made at different angles through the object, with separate images being recorded on separate films for each different angle, to produce a set of radiographs. The set of radiographs may then be superimposed in a stack for viewing and, with the radiographs aligned so that the images of a given point in the object all coincide, all other points or object details in the same plane, will be revealed in an unobstructed view; images of all points lying in other planes, even closely adjacent planes, will be obliterated. Assuming, for instance, the use of cut films with the image of a given point in the reference plane falling at the center of each film for each exposure angle, a virtual focus of the reference plane is achieved and the images of the given point are superimposed when the radiographs are superimposed directly on top of each other. If the given point lies between the reference plane and the film, the images of the given point on the respective radiographs will be superimposed and the plane through the given point will be brought into virtual focus when the radiographs are shifted relative to each other in one direction parallel to the tomographic movement, i.e. the track direction. On the other hand, if the given point lies between the reference plane and the source, the images of the given point will be superimposed with the respective radiographs shifted relative to each other in the opposite direction parallel to the tomographic movement. Any desired plane may be brought into virtual focus by relative shifting of the set of radiographs to superimpose the images of a point lying in the plane of interest. In this relationship of the radiographs, the multiple images on the different radiographs of the same point reinforce each other, while a given point in any other plane is imaged on different radiographs at nonaligned positions and the resulting image is, therefore, blurred to the extent that it merely forms a background for the points in the reference plane.

Although dynamic tomography is a proven and successful technique for demonstrating parallel planes through the depth of the body, it has heretofore been difficult to extend the principles of dynamic tomography to demonstrate other surfaces of different shape and orientation within the body. The earlier referenced Richards patent, U.S. Pat. No. 3,499,146, proposes a method for accomplishing the demonstration of arbitrary surfaces within a body. In particular, it requires that each of a plurality of laminar surfaces through the body be raster scanned. The scanned data is then digitized and electronically stored in accordance with a storage scheme that addresses each scan element in terms of the laminar image in which it appears and its position within that laminar image. In short, the scanning technique builds up a 3-dimensional Cartesian representation of the body. When an arbitrary surface is to be demonstrated, it is constructed by calling up the addresses of the scanning elements that represent the surface in the 3-dimensional representation of the body, and presenting them on a display. This method, while practicable, requires an extensive commitment in electronic scanning apparatus, storage means and display means for the demonstration of an arbitrary surface.

An objective of the present invention is, therefore, to extend the principles of dynamic tomography to provide a simplified manner of demonstrating and recording an arbitrary surface within a body.

DISCLOSURE OF THE INVENTION

The present invention is a method and apparatus for demonstrating and recording a surface of arbitrary shape and orientation within a body using the established technique of dynamic tomography.

Broadly, the invention contemplates employing the technique of dynamic tomography to prepare a set of radiographs or tomographic records taken from a radiographic examination of the body. These tomographic records are overlaid on one another in superimposed relation. The superimposed tomographic records are then shifted under operator control to bring into virtual focus a continuous succession of laminar planes through the depth of the body. As the image of each body plane comes into focus, it is exposed to a photoreceptive medium through a mask. The photoreceptive medium has motion relative to the tomographic records in timed relation to the shifting of the records. The mask has formed in it an aperture of shape and dimension corresponding to the arbitrary surface which is to be demonstrated. Specifically, the mask passes to the photoreceptive medium only that portion of the body image that represents the intersection of the arbitrary surface with the body plane in focus. Accordingly, when the operator has advanced the focusing through the depth of the body, the arbitrary surface to be demonstrated will have been developed on the photoreceptive medium.

A practical embodiment of the invention calls for the photoreceptive medium to be a photographic film. The photographic film is moved in timed relation to the shifting of the tomographic records to develop a proportional representation of the arbitrary surface to be demonstrated over the surface of the film. Moreover, the mask and photoreceptive medium may both be moved relative to the body planes to vary the orientation of the arbitrary surface to be demonstrated.

Alternative embodiments of the invention have a coherently-arranged array of optical fibers performing the role of the mask. Specifically, the optical fibers selectively transmit portions of the image of the body plane in focus to the surface of the photoreceptive medium. The photoreceptive medium could, for example, be an electronic scanner that scans the image transmitted by the mask and places the scanned information in electronic storage.

Other advantages of the present invention will be readily appreciated as the same becomes better understood by reference to the following detailed description when considered in connection with the accompanying drawings.

BRIEF DESCRIPTION OF DRAWINGS

FIG. 1 is a front elevational view of a radiograph viewer for use in accordance with the present invention;

FIG. 2 is a cross-sectional view of the radiograph viewer of FIG. 1 taken along lines 2—2;

FIG. 3 is an internal view of the radiograph viewer of FIG. 1 showing the film shift mechanism;

FIG. 4 is a schematic representation of the radiograph viewer of FIG. 1 in association with a viewing mask used to isolate a portion of the image on the viewer;

FIG. 5 is a schematic view of the geometric relation between the object appearing on the radiograph viewer and the viewing mask;

FIGS. 9, 10, 11 and 12 all relate to the demonstration of a body surface through use of a set of radiographs taken from a circular radiographic examination of the body or object;

FIG. 13 is a side sectional view of a film and mask transport apparatus that is useful in conjunction with the surface demonstration of FIG. 8; and FIG. 14 is a schematic representation of an array of optical fibers that could be used in place of the viewing mask to selectively communicate the image from the radiograph viewer to the film or other recording means.

BEST MODE FOR CARRYING OUT THE INVENTION

Figure 6:
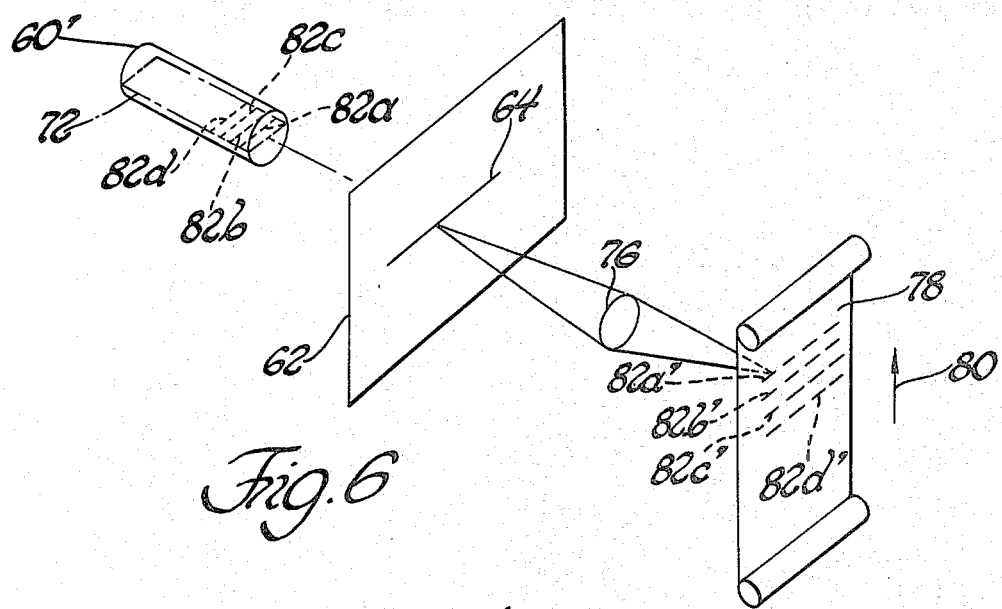
FIG 6 is a schematic representation of how the viewing mask is used to demonstrate or record an arbitrary surface of the object appearing in the radiograph viewer.

The present invention relates to dynamic tomography, and is directed to a method and apparatus whereby the established principles of dynamic tomography may be extended to allow a surface of arbitrary shape and orientation within a body to be demonstrated or recorded based on a set of radiographs or tomographic records taken from a radiographic examination of the body.

By way of background, the technique of dynamic tomography is briefly described as follows.

A body or object, animate or inanimate, is placed on a level surface, generally a table. A radiographic examination is then conducted of the body or object by exposing it to penetrating radiation, preferably X-rays, from a source moved sequentially through several discrete positions, and recording the resultant ray transmission pattern for each of the discrete positions. More specifically, the radiation source is positioned above the object or body, and a film holder is positioned below the body. The radiation source is moved through a sequence of discrete positions, and a radiological exposure of the body is made for each position. The radiation source and film holder move in corresponding relation such that the axis of the X-ray beam passes through an effective pivot point in or near the body for each respective positioning of the source and film holder. The resultant ray transmission pattern for each radiological exposure is recorded on a separate frame of film. The sequence of discrete positions that the radiation source is moved through may define a linear or non-linear path. In the case of a non-linear path, the path may take a circular, spiral, elliptical, hypocycloidal or similar type form.

The plurality of film records or radiographs taken from the radiographic examination of the body are then overlaid on one another in superimposed relation. The body may then be examined at various depths by shifting laterally the radiographs with respect to one another until all points lying in a specific plane are brought into aligned relationship with one another. This aligned condition brings the specific plane into virtual focus, and obliterates interfering shadows of other body planes.

In the case where the radiographic examination of the body has been taken along a linear path, a technique has been developed to facilitate viewing of the set of radiographs or tomographic records resulting from the examination. This technique is embodied in a method and apparatus described in U.S. Pat. No. 3,742,236, issued to Richards, June 26, 1973, and U.S. Pat. No. 3,830,128, issued to Cochran et al, issued Aug. 20, 1974, and is briefly described as follows.

In this technique the radiographs are formed on conventional X-ray film which is preferably rectangular cut film or suitable roll film in a conventional film holder. The radiographs are provided during exposure with data that represents sufficient information to define the proper orientation relative to the image and the angularity of a parallelogram, which will enable the relative shifting of the set of radiographs to select a desired plane for viewing. A pair of track markers, such as lead balls, are disposed adjacent the object and are on a line parallel to the movement of the radiation source, i.e. its track direction. A cross-marker is disposed in a plane nearer the X-ray source and is laterally offset from the track markers so that its image falls on the film in a position relative to one of the track markers so that the line therethrough defines an angle indicative of or corresponding to the angle of exposure of the film. After development of the film, the images of the track markers define a line in a direction of track motion and hence the direction of relative shifting which the radiographs must undergo in the selection of a given plane for viewing. Accordingly, the film is cut with "reference sides" parallel to the track line and spaced a fixed distance apart, i.e. at constant altitude. The image of the cross-marker and one of the track markers enables the establishment of a line which corresponds to the angularity and which enables the "angle sides" of the parallelogram to be cut parallel thereto. The "angle sides" of all of the films of a given set have different angles relative to the reference sides and are spaced apart a fixed width.

Assuming a set of radiographs or tomographic records of a body have been developed and cut into parallelogram form in accordance with the foregoing method, the discussion now proceeds to a description of how the radiographs can be used in the present invention to demonstrate or record a surface of arbitrary shape and orientation within the body. The term "arbitrary" in this context includes surfaces that are not necessarily parallel to the plane in which the film holder was disposed, that heretofore being a limitation of conventional dynamic tomography.

A radiograph viewer for films cut into parallelograms in accordance with the previously described method is shown in FIGS. 1, 2 and 3. The viewer 10 comprises a housing 12 including a front panel 14, having a rectangular glass plate 16 mounted therein. The glass plate 16 is preferably a light diffusing type material. A light source 18 is mounted within the housing 12 and is adapted to be electrically energized. A heat absorbing glass plate 20 is disposed between the light source 18 and the diffusing glass 16.

The front panel 14 is provided with a pair of guides 22 and 24 which extend vertically and are spaced apart a distance equal to the altitude of the parallel films. A pair of runners 26 and 28 are mounted on the face of the panel in respective guide channels 30 and 32 which extend laterally across the width of the glass plate 16. The runners 26 and 28 are disposed opposite each other in a vertical plane and include, respectively, cam elements 34 and 36 for movement in unison across the width of the plate 16. A set of parallelogram films 38, which may be superimposed or stacked together in any desired order, are placed on the face of the viewer 10 with the reference sides disposed between and engaging the guides 22 and 24, and with the angle sides disposed between and engaged by the cam elements 34 and 36.

In order to move the runners 26 and 28 in unison across the glass plate 16 for the purpose of shifting the films in the set 38, a cable drive, including a manual knob 40 on the front panel 14 is provided. As shown best in FIGS. 2 and 3, the knob 40 is connected by a shaft 41 to a drive pulley 42. A continuous drive cable 44 is driven by the drive pulley 42. The drive cable 44 extends from the drive pulley 42 to a lower pulley 46 and thence upwardly to a first upper pulley 48 and across to a second upper pulley 50. From upper pulley 50 the cable continues downwardly to a first intermediate pulley 52 and thence across to a second intermediate pulley 54 and back across the first intermediate pulley 52. From the intermediate pulley 52, the cable 44 then extends downwardly to a second lower pulley 56, and finally returns to the drive pulley 42.

The upper runner 26 is connected to the cable 44 in the span between the first and second upper pulleys 48 and 50. The lower runner 28 is attached to the cable 44 in the span between the intermediate pulleys 52 and 54. The spacing of the upper and lower runners 26 and 28 is such that they are always in vertical alignment. When the knob is rotated in a clockwise direction, the runners 26 and 28 move in unison from left to right, and when the knob 40 is rotated in a counterclockwise direction, the runners move from right to left.

In operation of the viewer 10, the set 38 of parallelogram films is stacked in any order and placed on the front panel 14 of the viewer between the guides 22 and 24 and between the cam elements 34 and 36. With the light source 18 energized, the films are back lighted and the radiographs thereon may be viewed. The image of any selected plane within the object or body having a parallel relation to the plane in which the film holder was disposed may be brought into virtual focus by rotating the manual knob 40. Rotation of the knob causes the runners 26 and 28 to move laterally and the cam elements 34 and 36 mounted thereon are effective to shift the films in the set 38 relative to each other, whereby the desired plane may be selected for viewing.

FIG. 4 is a schematic representation of the radiograph viewer 10 in association with a viewing mask 62 used in accordance with the present invention to demonstrate an arbitrary surface. The viewer 10 has displayed on it a superimposed set of radiographs or tomographic records 38 taken of an object 60. A viewing mask 62, which functions as an image selection means, is placed adjacent and parallel to the front surface or screen of the viewer 10. The viewing mask 62 has formed in it an aperture 64 that selectively transmits only a portion of the image of the object 60.

FIG. 5 is a geometric model of the viewer 10, object 60 and mask 62 of FIG. 4, and is useful as an aid in analyzing the principles of the present invention.

The object or body recorded on the tomographic record is spatially represented as a right cylinder 60' having its axis perpendicular to the front plane 66 of the viewer. The body surface to be demonstrated is a planar section 72 lying in a plane 68 that contains the axis of the cylinder 60' and is perpendicular to the front plane 66 of the viewer. The plane of the viewing mask is represented by a plane 70 that is spaced apart from and parallel to the plane 66. The body surface 72 will be demonstrated by bringing into virtual focus images of successive levels or planes, as exemplified by 74a, b and c, through the depth of the body 60'. The viewing mask will serve to block or screen all but the portion of each focused image that represents the intersection of the body surface 72 with the image of the body plane in focus.

This analysis is now applied to the demonstration and recordation of a body surface in the manner illustrated in FIG. 6. The surface 72 of the body 60' is to be demonstrated and recorded on a roll of photographic film 78. Accordingly, a continual succession of body planes or laminae of the body 60' are brought into virtual focus by laterally shifting a set of radiographs taken of the body 60'. As the image of each body plane comes into virtual focus, only that part of the image that represents the intersection of the body surface 72 with the imaged plane in focus is allowed to pass through the aperture 64 in the mask 62. A lens 76 focuses the transmitted light energy onto the surface of the photographic film 78. The photographic film 78 is transported upwardly as indicated by arrow 80. The transportation of the film 78 is in timed relation to the lateral shifting of the radiographs or tomographic records representing the body 60'. If the lateral shifting of the radiographs is done in such a manner that the virtual focusing of body planes progresses from the front face to the rear face of the body 60', then successive lines over the length of the body surface 72, as exemplified by lines 82a, b, c and d, will correspondingly appear as lines 82a', b', c' and d' on the photographic film 78. This process produces a full exposure on the film 78 of the body surface 72, which in the present example is a plane perpendicular to the front surface of the cylinder 60'.

Figure 7:
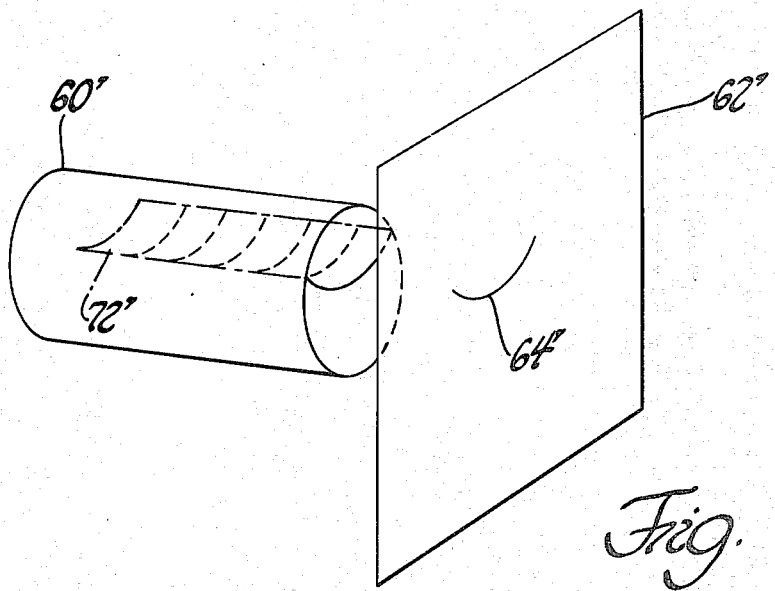
FIG. 7 is an alternative embodiment of the viewing mask of FIGS. 4, 5 and 6, showing a curvilinear aperture which would be used for the demonstration of nonplanar body surfaces.

FIG. 7 illustrates how a curved body surface 72', other than a planar body surface through the body 60', may be demonstrated. In this case, a viewing mask 62' has formed in it an aperture 64' that represents the curved line defined by the intersection of a plane perpendicular to the axis of the curved body surface 72' with the body surface. The entire curved body surface 72' may be produced and recorded on photographic film by substituting the mask 62' for the mask 62 in the arrangement of FIG. 6.

Figure 8:
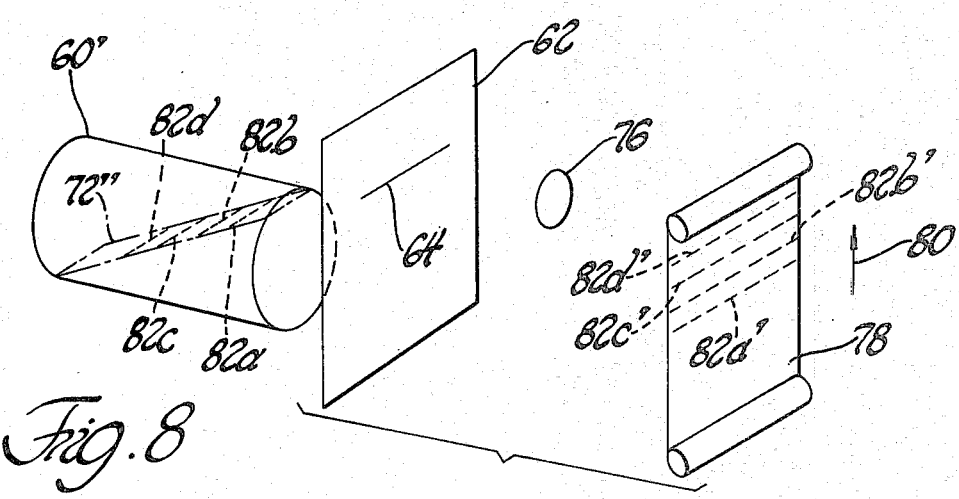
FIG. 8 is a schematic representation of how a body surface having a skewed axis with respect to the orthogonal axes of the body or object would be demonstrated.

FIG. 8 illustrates the manner in which a body surface 72" that has its axis at an acute angle with respect to the end faces of the right cylinder 60', and more precisely to the plane of the tomographic records containing the right cylinder images, may be demonstrated and recorded. In this case, the mask 62 and lens 76 are transported downwardly together with the photographic film 78, in the direction indicated by arrow 80. The transportation of the mask 62, lens 76 and film 78 is in timed relation to the lateral shifting of the tomographic records representing the body 60'. With the correlated movement of the mask 62 and film 78, the lines on the body surface 72" identified as 82a, b, c and d, will correspondingly appear on the film in the positions indicated by lines 82a', b', c' and d'. This process of simultaneous movement of the mask 62 and film 78 allows a full exposure on the film 78 of a body surface, such as surface 72", which is oriented at an acute angle with respect to the plane of the tomographic records containing the body images.

FIG. 13 illustrates a transport mechanism 150 by which the correlated transportation of the photographic film 78 and viewing mask 62 may be accomplished. The transport mechanism 150 includes a housing 152 which encloses internal transport apparatus. External to the housing 152 is a wheel 154, either a thumbwheel or pulley, which provides a means for driving the internal transport apparatus. A drive shaft 156 is connected to the wheel 154 and is journaled in the frame of the housing and drivingly connected with a pair of drive pulleys 158 and 160. At the end of the drive shaft 156 opposite the external wheel 154, is another wheel 162 that may be mechanically coupled to the operator control wheel 40 of the radiograph viewer 10 of FIG. 1 to synchronize the lateral shifting of the radiographs with the transportation of the mask 62 and film 78.

The drive pulley 158 is coupled to a driven pulley 166 through a convoluted belt 164. A film take-up roller 168 is mounted coaxially with the driven pulley 166. A film feed roller 170 is driven by the rotation of the take-up roller 168. Photographic film that is initially wound on feed roller 170 is fed in a continuous web 78 to the take-up roller 168.

The drive pulley 160 is mechanically coupled to a driven pulley 174 by a convoluted belt 172. A mask take-up roller 176 is mounted coaxially with the driven pulley 174. A mask feed roller 178 is driven by the rotation of the take-up roller 176. The mask 62 is transported from the feed roller 178 to the take-up roller 176 to cause the mask aperture (not shown) to scan over the body image. The mask is preferably formed of opaque sheet material with sufficient flexibility to allow it to be wound upon rollers 176 and 178.

When the film 78 and mask 62 are transported downwardly together, as in the present example, the image of the body surface will appear in inverted form on the film 78. An alternative arrangement could have the film 78 and mask 62 transported in mutually opposite directions to produce a non-inverted image.

The driving of the mask 62 and the film 78 by the common shaft 156 causes the mask and film to be transported in correlation with one another. Moreover the transportation of the film and mask is in timed relation to the shifting of the radiographs in the viewer.

Dynamic tomography may also be accomplished with a radiographic examination of the body taken through a non-linear path, e.g. a circular, spiral, elliptical or hypocycloidal path. In order to view radiographs taken from a non-linear radiographic examination, it is necessary that the radiographs be shifted in accordance with the character of the non-linear path. In the case of a circular examination path, the superimposed radiographs would each have to be shifted radially with respect to one another to bring into virtual focus images of successive body levels. This is to be contrasted with the viewing of radiographs taken from a linear examination path, which merely require lateral or one-dimensional shifting.

For this purpose a radiograph viewer designed for radiographs taken from a circular examination path is shown in FIGS. 9, 10 and 11. The subject radiograph viewer is fully disclosed in U.S. Pat. No. 3,818,220, issued to A. G. Richards, June 18, 1974. A brief description of the structure and operation of the circular radiograph viewer will be given herein to show its adaptability for use in conjunction with the present invention.

With particular reference to FIG. 9, the circular radiograph viewer 100 includes a base plate 110 supported in opposed brackets 112 stabilized by side plates 114. On the base plate 110 is a flat ring 116 fixed to the base plate and carrying a plurality of eight pins 118. The ring 116 has an opening 120 which serves as a light window. An outer actuator ring 122 is mounted on the base plate 110 for rotational movement around the ring 116. The outer actuator ring 122 is held captive on the flat ring 116 by a diametrically opposed pair of overlap flanges 124, each of the flanges forming part of an associated bracket 112.

With reference to FIG. 10, the base plate 110 is provided with a series of radial surface slots 130. In each of the radial surface slots is mounted a slide block 132 that carries an upright pin 134. Each of the upright pins 134 passes through a curved slot 136 formed in circumferentially spaced relation around the outer actuator ring 122. It will thus be seen that rotation of the outer actuator ring 122 relative to the flat ring 116 in the base plate 110 will cause the slide blocks 132 to move radially inward or outward depending on the direction of rotation, and such motion of the slide blocks will carry the upright pins 134 in the same radial direction.

FIG. 11 is a side view of the assembly of FIG. 9 illustrating the manner in which circular radiographs are viewed by an observer. For ease of explanation, it is assumed that only two circular radiographs 102 and 104 are mounted on the radiograph viewer 100 of FIG. 11, although the viewer can normally accommodate a set of eight radiographs. As best shown in FIG. 12, each of the radiograph frames 102 and 104 has an elongate rectangular shape with a longitudinal axis. Each frame 102 and 104 is provided with a first aperture 101 in the form of a circular hole proximate one end of the longitudinal axis, a second aperture 103 in the form of a slot proximate the other end of the longitudinal axis, and a third aperture 105 in the form of a slot lying along the longitudinal axis proximate the first aperture and distal the second aperture. The radiograph frame 102 has its first and third apertures 101 and 105 perforated by a pair of diametrically opposed pins 118, and its second aperture perforated by an upright pin 134. The second radiograph frame 104 is disposed with its longitudinal axis perpendicular to the longitudinal axis of frame 102. The second frame similarly has its first, second and third apertures perforated by pins 118 and 134 in the manner of frame 102. Thus, the radiograph frames 102 and 104 will be guided on the pins 118, and the pin 134 in each case will serve as the actuator pin that will shift the film diametrically across the window opening 120. Accordingly, it will be seen that rotation of ring 120 relative to the base plate 110 will cause the radiograph frames 102 and 104 to move at right angles to each other in a sliding relationship.

A light source 150 directs light to the window 120 where an observer may view the overlapping frames 102 and 104 as they are shifted relative to each other. The cross shifting of the frames will produce various tomographic views depending on the relative position of the frames, and thereby delineate respective body planes through the radiographed object depending on such relative position. Each of the delineated body planes will have a parallel relation to the plane of the tomographic records 102 and 104.

FIG. 12 schematically illustrates the principles of circular tomography applied in the context of the present invention. The two circular radiograph frames 102 and 104 are shown in association with a mask 62 having an aperture in the form of a narrow horizontal slit 64. The function of the mask in this context is no different from its function in the case of linear dynamic tomography. Specifically, it serves to transmit only that portion of the image appearing in focus on the viewer screen that represents the intersection of the body surface to be demonstrated with the image of the body lamina in focus.

The portion of the image not masked out by the mask 62 is transmitted through a lens system 76 onto a photographic film 78 in the manner heretofore described. The invention is also adaptable to contact printing, i.e. where the lens 76 is not used and the mask 62 and film 78 are laid directly on the outer-most radiograph for direct imaging.

The masking function may be performed by other than the specific mask structure previously described herein. One practicable alternative is to use a linear array of coherently-arranged, optical fibers as is schematically illustrated. A linear optical fiber array 180 has a first end 182 in light communication with the image appearing on the viewer, and a second end 184 in light communication with a photosensitive recording medium, generally photographic film. The fibers in the array 180 are arranged to selectively transmit only that portion of the focused image that would be ordinarily transmitted by an apertured mask. The fiber optic array has the advantage of the ability to transmit an image from its first surface 182 to the second surface 184 around curves and into otherwise inaccessible places within an extremely low loss of definition and light by a process of total reflection.

Moreover, the invention may be practiced with a number of photoreceptive media in addition to photographic film. For example, the photoreceptive medium could be an electronic recording device, photoconductive surface as used in xerographic printing, video tape, etcetera. The disclosure of the invention by means of photographic film is merely exemplary.

The invention has been described in an illustrative manner, and it is to be understood that the terminology which has been used is intended to be in the nature of words of description rather than of limitation.

Many modifications and variations of the present invention are possible in light of the above teachings. It is, therefore, to be understood that within the scope of the appended claims, the invention may be practiced otherwise than as specifically described.

What is claimed is:

1. A method for producing an image of a surface of arbitrary shape and orientation within a body from a set of tomographic records taken from a radiographic examination of the body, the method comprising the steps of:
   (a) superimposing the set of tomographic records in overlying relation with one another;
   (b) shifting each of the tomographic records with respect to one another to bring into virtual focus a continuous succession of laminar images through the depth of the body; and
   (c) selecting a predetermined portion of each of the focused laminar images that represents the intersection of the body surface to be produced with the image of the lamina in focus, whereby the arbitrary surface is produced by the continuous succession of focusing of laminae through the depth of the body.

2. The invention as defined in claim 1 wherein step (c) includes the step of masking all but that portion of each of the focused laminar images that represents the intersection of the body surface to be produced with the image lamina in focus.

3. The invention as defined in claim 1, including the further step of recording the selected portion of each focused laminar image to form a composite record of the arbitrary body surface.

4. The invention as defined in claim 3, wherein the recording of the body surface comprises the steps of (i) exposing the selected portion of each focused laminar image onto a photoreceptive medium, and (ii) moving the photoreceptive medium in timed relation to the shifting of the tomographic records.

5. Apparatus for producing an image of a surface of arbitrary shape and orientation within a body from a set of tomographic records taken from a radiographic examination of the body, the apparatus comprising:
   viewer means for supporting the set of tomographic records in superimposed relation, and responsive to operator control to shift each of the tomographic records in concert with respect to one another to bring into virtual focus a continuous succession of laminar images through the depth of the body; and
   image selection means for selecting a predetermined portion of each of the focused laminar images that represents the intersection of the body surface to be produced with the image of the lamina in focus, whereby an image of the arbitrary surface is produced by the continuous succession of focusing of laminae through the depth of the body.

6. The invention as defined in claim 5, wherein the image selection means comprises a planar mask positioned in close proximity to the viewer means in a plane substantially parallel to the tomographic records, the planar mask having an aperture formed therein corresponding to the shape and dimension of the body surface to be produced.

7. The invention as defined in claim 6 wherein the aperture is defined by a linear slit.

8. The invention as defined in claim 6, wherein the aperture is defined by a curvilinear slit.

9. The invention as defined in claim 5, further including recorder means for recording the image of the arbitrary surface.

10. The invention as defined in claim 9, wherein the recorder means comprises a photoreceptive medium.

11. The invention as defined in claim 10, wherein the recorder means further comprises means for moving the photoreceptive medium relative to the viewer means and in timed relation to the shifting of the tomographic records.

12. The invention as defined in claim 10, wherein the photoreceptive medium comprises photographic film.

13. The invention as defined in claim 5, further including means for moving the image selection means relative to the viewer means and in timed relation to the shifting of the tomographic records.

14. The invention as defined in claim 5, wherein the image selection means comprises an array of optical fibers.

15. The invention as defined in claim 14, wherein the array of optical fibers is coherently-arranged.

* * * * *